(12) United States Patent
Zhang et al.

(10) Patent No.: US 11,925,708 B1
(45) Date of Patent: Mar. 12, 2024

(54) METHOD FOR MAKING MODIFIED POLYVINYL ALCOHOL EMBOLIC MICROSPHERE

(71) Applicant: JIANGNAN UNIVERSITY, Wuxi (CN)

(72) Inventors: Liping Zhang, Wuxi (CN); Yi Zhu, Wuxi (CN); Wenlong Wang, Wuxi (CN); Caihua Ni, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 18/049,244

(22) Filed: Oct. 24, 2022

(30) Foreign Application Priority Data

Sep. 23, 2022 (CN) .......................... 202211169477.3

(51) Int. Cl.
| | |
|---|---|
| *C08F 116/06* | (2006.01) |
| *A61K 9/00* | (2006.01) |
| *A61K 9/16* | (2006.01) |
| *A61K 31/585* | (2006.01) |
| *A61K 45/06* | (2006.01) |
| *A61K 47/32* | (2006.01) |
| *A61K 49/04* | (2006.01) |
| *A61L 24/00* | (2006.01) |
| *A61L 24/04* | (2006.01) |
| *A61L 24/06* | (2006.01) |
| *A61L 24/10* | (2006.01) |
| *B82Y 5/00* | (2011.01) |
| *C08F 2/48* | (2006.01) |
| *C08F 8/14* | (2006.01) |
| *C08F 8/36* | (2006.01) |
| *C08F 220/58* | (2006.01) |
| *C08F 222/38* | (2006.01) |
| *C08F 226/10* | (2006.01) |
| *C08F 261/04* | (2006.01) |
| *C08L 59/04* | (2006.01) |

(52) U.S. Cl.
CPC .......... *A61K 9/1682* (2013.01); *A61K 9/1635* (2013.01)

(58) Field of Classification Search
CPC ........................... A61K 9/1682; A61K 9/1635
See application file for complete search history.

(56) References Cited

U.S. PATENT DOCUMENTS 10,406,257 B2 * 9/2019 Dreher ................ A61L 24/0031

FOREIGN PATENT DOCUMENTS

| CN | 103613718 A | 3/2014 |
| CN | 103977458 A | 8/2014 |
| CN | 106729953 A | 5/2017 |

* cited by examiner

*Primary Examiner* — Tracy Liu
*Assistant Examiner* — Abdulrahman Abbas
(74) *Attorney, Agent, or Firm* — HAUPTMAN HAM, LLP

(57) ABSTRACT

The invention provides a making method of modified polyvinyl alcohol embolic microspheres. First, polyvinyl alcohol dimethyl sulfoxide solution is added to acryloyl chloride dichloromethane solution for reaction, then taurine solution is added to the above solution for further reaction, so that functional groups are introduced into the side chains of polyvinyl alcohol, then blank microspheres are prepared by suspension crosslinking method, and finally, drug-loaded modified polyvinyl alcohol embolic microspheres are prepared. The invention aims at improving the drug loading rate and drug loading speed of the microspheres. Through modification, the crystallinity of polyvinyl alcohol is weakened, the swelling in water is accelerated, and the application effect of the microspheres is improved.

9 Claims, 3 Drawing Sheets

METHOD FOR MAKING MODIFIED POLYVINYL ALCOHOL EMBOLIC MICROSPHERE

RELATED APPLICATIONS

The present application claims priority from Chinese Application Number 202211169477.3, filed Sep. 23, 2022, the disclosure of which is hereby incorporated by reference herein in its entirety.

1. TECHNICAL FIELD

The invention relates to a making method of modified polyvinyl alcohol embolic microspheres thereof, belonging to the technical field of polyvinyl alcohol modification and medical materials.

2. BACKGROUND ART

Embolized microspheres play an important role in interventional therapy for malignant tumors. Embolized microspheres are introduced selectively into blood vessels near by tumors through catheters in minimally invasive vascular surgery, and cut off the supply of nutrition and oxygen to organs, tissues or tumors through blocking blood flow, thereby inhibiting tumor growth.

At present, the known embolic microspheres include polyvinyl alcohol microspheres, gelatin microspheres, ethylcellulose microspheres, albumin microspheres, polylactic acid microspheres and chitosan microspheres. Most of these are non drug loaded microspheres, which can only play the role of mechanical embolism and cannot load drugs. Drug-loaded embolic microspheres contain certain amount of functional groups which can interact with chemotherapeutic drugs, therefore, the drugs can be loaded on the microspheres. The drug-loaded microspheres can not only block arterial blood supply, but also make chemotherapeutic drugs release directionally.

Polyvinyl alcohol (PVA) is a water-soluble linear polymer. It is a macromolecular organic material. It is cheap, easy to synthesize, non-toxic to human body, therefore, it is widely used in the biomedical fields due to its safety, good biocompatibility, excellent flexibility and thermal stability. For example, polyvinyl alcohol hydrogels can be used as wound dressings, artificial joints and ophthalmology, and polyvinyl alcohol can also be used to prepare embolic microspheres, some of which have been commercialized.

The unmodified PVA microspheres have no good functional groups and lack effective loading contents for charged anticancer drug molecules. In addition, the crystallinity of polyvinyl alcohol is strong. So the pure polyvinyl alcohol microspheres swell slowly in water with low swelling ratios, the hardness of the microspheres is strong, leading to poor use performance of the microspheres.

In the past, the graft polymerization of 2-acrylamido-2-methylpropanesulfonic acid (AMPS) was adopted for modification of polyvinyl alcohol. However, the molecular weight of 2-acrylamido-2-methylpropanesulfonic acid was large, the degree of graft polymerization in the side chain of polyvinyl alcohol was low, the content of sulfonic acid groups obtained was not high, and the drug loading effect was not ideal.

There are also patent reports that some modified polyvinyl alcohol microspheres have been prepared through surface modification of blank PVA microspheres. However, when the PVA microspheres are functionalized on the surface, the functional groups are located only on the surface of the microspheres, the number of the functional groups is still small, and the internal crystallinity of the microspheres is strong, the hardness of the microspheres is large, the swelling is difficult, and the use effect is not good.

It is also reported in the patent that crosslinkers containing functional carboxyl or sulfonic acid groups are prepared in advance, and then the functional groups are introduced into polyvinyl alcohol through copolymerization. But the related synthetic method is complex, and the content of introduced functional groups is not high.

SUMMARY OF THE INVENTION

In order to overcome the shortcomings of the current PVA embolic microspheres, the invention provides a making method of PVA embolic microspheres. Firstly, the hydroxyl groups in PVA structural units are modified by sulfonic acid groups which link to side chains of PVA directly, and the modified polyvinyl alcohol is prepared. Then microspheres are prepared based on the modified polyvinyl alcohol as a material, and finally the drug loaded modified PVA embolic microspheres are prepared. The invention aims at improving the drug loading rate and drug loading speed of the microspheres. After the modification, the crystallinity of the polyvinyl alcohol is weakened, the swelling in water is accelerated, and the swelling degree is improved.

To achieve the above purpose, a making method of modified polyvinyl alcohol embolic microspheres adopted by the invention is as follows:

Step 1: putting polyvinyl alcohol in organic solvent A, stirring for dissolving the PVA, and preparing polyvinyl alcohol solution; dissolving acryloyl chloride or butylenoyl chloride in organic solvent B to prepare an acyl chloride solution;

Specifically, the organic solvent A is one of dimethyl sulfoxide, N, N-dimethylacetamide or formamide; the organic solvent B is one of dichloromethane, trichloromethane or dichloroethane; The polyvinyl alcohol brand is one of PVA124, PVA1799, PVA1750 and PVA1788; The concentration of polyvinyl alcohol solution is 50-120 g/L; The concentration of acyl chloride solution is 80-150 g/L.

Step 2: adding acid binding agent to the polyvinyl alcohol solution, dropping the above acyl chloride solution into the polyvinyl alcohol solution, stirring for 3-5 hours at the room temperature, then heating up to 4550° C., continue stirring and reacting for 1-2 hours, cooling down to the room temperature, pouring the reaction solution into excess absolute ethanol for precipitating the polymer, filtering, washing the polymer with absolute ethanol, drying to a constant weight, to obtain allyl polyvinyl alcohol or butyryl polyvinyl alcohol.

Specifically, the molar ratio of the PVA (according to the structural unit) to the propylene (or butene) acyl chloride is 1:0.2-1; the acid binding agent is triethylamine or pyridine, and its dosage is 1-1.2 times of the molar number of propylene (or butene) acyl chloride.

Step 3: weighing the dry allyl polyvinyl alcohol or butyryl polyvinyl alcohol and putting them in water, stirring and dissolving them; then dissolving taurine in water, adding it to allyl polyvinyl alcohol or butyryl polyvinyl alcohol solution, adjusting the pH value to 9-11, stirring it at 4550° C., continue reacting for 4048 hours, and then cooling it to the room temperature, pouring the reaction solution into excess absolute ethanol slowly, filtering and washing the polymer with absolute ethanol, and finally drying the polymer in an oven to a constant weight, to obtain the functionalized modified polyvinyl alcohol;

Specifically, the molar ratio of the acryloyl chloride to the taurine is 1:1-1.3 in the feed.

Step 4: adding non-ionic surfactant to an oil phase solution, and stirring evenly; in addition, dissolving the above functionalized modified polyvinyl alcohol in water to prepare a PVA solution with a concentration of 60-100 g/L; then slowly pouring the PVA solution into the above oil phase solution for emulsification. When Tyndall phenomenon is observed in the emulsion, dropping a cross-linking agent to the emulsion. After 4-6 hours reaction, demulsifying the emulsion to obtain solid microspheres, washing the microspheres with ethanol and drying the microspheres to obtain modified polyvinyl alcohol embolic microspheres. Specifically, the oil phase solution is selected from one of paraffin oil, soybean oil or n-heptane; the non-ionic surfactant is selected from one of Span 80, Tween 2080 and NP-10; the volume ratio of the modified polyvinyl alcohol solution to the oil phase solution is 1:4-7; the cross-linking agent is glutaraldehyde solution or epichlorohydrin, and its weight accounts for 3-6% of the weight of functionalized modified polyvinyl alcohol.

In addition, the invention also provides an application of the modified polyvinyl alcohol embolic microspheres. The modified polyvinyl alcohol embolic microspheres are prepared with the method above, and the modified polyvinyl alcohol embolic microsphere are loaded with doxorubicin hydrochloride to prepare drug-loaded modified polyvinyl alcohol embolic microspheres. Specifically, the modified polyvinyl alcohol embolic microspheres obtained above are placed into the doxorubicin hydrochloride solution for drug loading. The drug-loaded microspheres are separated by filtration, and the surface of the microspheres is washed with deionized water. Finally, the drug-loaded embolic microspheres can be obtained after drying.

With the above scheme, the invention has at least the following advantages:

First, polyvinyl alcohol is modified in a solution. When the polyvinyl alcohol molecule is in the solution state, it has sufficient contact with the reactants, uniform reaction and high reaction degree. The density of the functional groups in the modified polyvinyl alcohol embolic microspheres is high, which results in high drug loading rates.

Secondly, through the introduction of small molecules containing functional groups into the side chain of polyvinyl alcohol, the crystallinity is weakened, so the swelling speed and swelling degree of the microspheres in water are accelerated, which is also conducive to improve the drug loading speed and drug loading rate of microspheres. Finally, taurine is used as a functional monomer and introduced into the side chain of polyvinyl alcohol. Taurine has small molecular weight and high reaction degree, which can effectively improve the density of functional groups in the microspheres, leading to improving the drug-loading.

DESCRIPTION OF PREFERRED EMBODIMENTS

Embodiment 1

Figure 1:
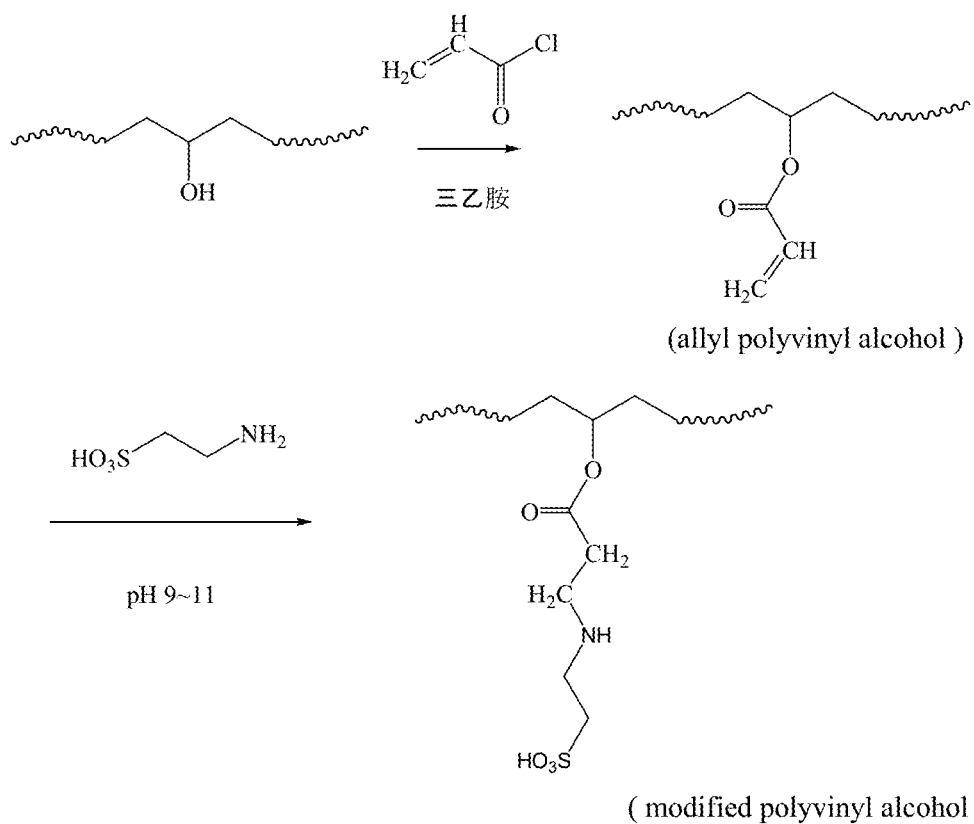
FIG. 1 Schematic route of the modified polyvinyl alcohol

The detailed implementation of the invention is further described as follows. The following embodiments are used to illustrate the invention, but not to limit the scope of the invention.

Step 1): 5 g of polyvinyl alcohol (PVA124) is dissolved in 50 mL dimethyl sulfoxide under stirring to prepare polyvinyl alcohol solution with a concentration of 100 g/L; 10 g of acryloyl chloride is dissolved in 100 mL of dichloromethane to prepare an acryloyl chloride solution with a concentration of 100 g/L;

Step 2): 50 mL polyvinyl alcohol solution of the step 1 (containing 0.1136 mol PVA) and 2.3 g of triethylamine are added into a 250 mL a three-necked flask; 20.57 mL acryloyl chloride solution of the step 1 (including 0.0227 mol of acryloyl chloride) is dropped into the polyvinyl alcohol solution through a constant pressure drop funnel under stirring at the room temperature for 3 hours, then the temperature is raised to for further reaction one hour, then decrease to room temperature. The reaction solution is slowly poured into excess absolute ethanol for precipitating polymer. The polymer is filtered, washed with absolute ethanol, and dried in at 45° C. to constant weight, allyl polyvinyl alcohol is obtained.

Step 3): The allyl polyvinyl alcohol from the above is putted into 100 mL deionized water under stirring for dissolution; 3.41 g (0.0273 mo) of taurine is dissolved in 100 mL deionized water, and is added to the allyl polyvinyl alcohol solution, adjusting pH 9-11, the reaction is carried out at 4550° C. under stirring for 48 hours; the reaction solution is slowly poured into excess absolute ethanol at the room temperature; the product is precipitated, filtrated, washed with absolute ethanol for three times, and finally dried to constant weight. The modified polyvinyl alcohol is obtained, and the grafting rate (Rg) is calculated according to the following formula:

$$R_g(\%) = \frac{W_D - W_{PVA}}{W_{PVA}} \times 100$$

Where $W_D$ is weight (g) of the dried modified polyvinyl alcohol, and $W_{PVA}$ is weight (g) of the unmodified polyvinyl alcohol, respectively.

Step 4): Preparation of embolic microspheres 200 mL of paraffin oil is putted into a beaker containing span-80 under stirring evenly; the functionalized modified polyvinyl alcohol is dissolved in 50 mL of deionized water to prepare a PVA solution with a concentration of 100 g/L in advance; then the PVA solution is slowly poured into the paraffin oil under strong mechanical agitation for emulsifying the solution. When Tyndall phenomenon is observed in the emulsion, 1.4 g of glutaraldehyde solution with a concentration of 25 wt % and 1.2 mL of 10 wt % hydrochloric acid are added. The crosslinking reaction is carried out for 4 h at the room temperature, then solid microspheres can be observed after demulsification of the emulsion. The microspheres are filtrated and washed with ethanol for three times.

After drying, the modified polyvinyl alcohol eluting microspheres can be obtained. The product symbol is PVA-S-1.

Embodiment 2

The preparation procedure is similar to Embodiment 1, excepting:
in step 2), changing the addition of triethylamine to 4.6 g; changing the addition of acryloyl chloride solution to 41.14 mL; in step 3), changing the addition of taurine to 6.81 g. The remaining procedures are the same as those in Embodiment 1, to obtain the modified polyvinyl alcohol eluting microspheres with the symbol PVA-S-2.

Embodiment 3

The preparation procedure is similar to Embodiment 1, excepting:
in step 2), changing the addition of triethylamine to 6.9 g; changing the addition of acryloyl chloride solution to 61.71 mL; in step 3), changing the addition of taurine to 10.21 g. The remaining procedures are the same as those in Embodiment 1, to obtain the modified polyvinyl alcohol eluting microspheres with the symbol PVA-S-3.

Embodiment 4

The preparation procedure is similar to Embodiment 1, excepting:
in step 2), changing the addition of triethylamine to 9.2 g; changing the addition of acryloyl chloride solution to 82.28 mL; in step 3), changing the addition of taurine to 13.62 g. The remaining procedures are the same as those in Embodiment 1, to obtain the modified polyvinyl alcohol eluting microspheres with the symbol PVA-S-4.

Embodiment 5

The preparation procedure is similar to Embodiment 1, excepting:
in step 2), changing the addition of triethylamine to 11.5 g; changing the addition of acryloyl chloride solution to 102.85 mL; in step 3), changing the addition of taurine to 17.25 g. The remaining procedures are the same as those in Embodiment 1, to obtain the modified polyvinyl alcohol eluting microspheres with the symbol PVA-S-5.

TABLE 1

Preparation formula of modified PVA embolic microspheres

| Sample | PVA solution[a] (mL) | acryloyl chloride solution[b] (mL) | triethylamine (g) | taurine (g) | grafting rate (%) |
|---|---|---|---|---|---|
| Embodiment 1 | 50 | 20.57 | 2.3 | 3.41 | 12.1 |
| Embodiment 2 | 50 | 41.14 | 4.6 | 6.81 | 17.8 |
| Embodiment 3 | 50 | 61.71 | 6.9 | 10.21 | 21.5 |
| Embodiment 4 | 50 | 82.28 | 9.2 | 13.62 | 24.6 |
| Embodiment 5 | 50 | 102.85 | 11.5 | 17.25 | 28.5 |

[a]Polyvinyl alcohol solution with concentration of 100 g/L;
[b]Acryloyl chloride solution with concentration of 100 g/L;

Embodiment 6: Comparative Embodiment

Preparation of pure polyvinyl alcohol microspheres: adding 200 mL paraffin oil into a 500 mL beaker, dropping 1.9 g of span-80 under mechanical stirring evenly; dissolving 5 g of polyvinyl alcohol (PVA124) in 50 mL of deionized water, then slowly pouring it into the above paraffin oil, emulsifying it with strong mechanical agitation.

When Tyndall phenomenon is observed in the emulsion, dropping 1.4 g of glutaraldehyde solution with a concentration of 25 wt %, and then dropping 1.2 mL of hydrochloric acid with a concentration of 10 wt %; after reaction for 4 h, demulsifying the emulsion and washing the microspheres with ethanol, to obtain pure polyvinyl alcohol microspheres after drying, with the sample symbol PVA.

Embodiment 7 Characterization of the Modified Polyvinyl Alcohol Eluting

Microspheres
1. Infrared Spectra

Figure 2:
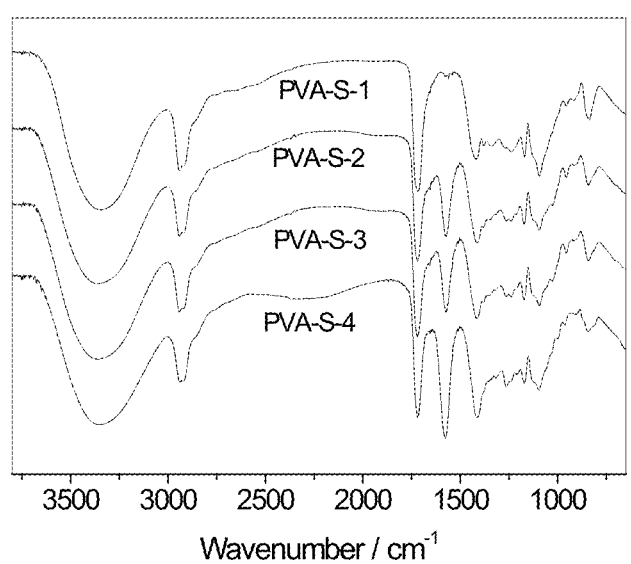
FIG. 2 Infrared spectra of the modified polyvinyl alcohol

The prepared modified polyvinyl alcohol embolic microspheres are dried and characterized by total reflection Fourier infrared spectroscopy, with a scanning range of 4000~500 cm$^{-1}$. It can be seen from FIG. 2 of the drawings that the 3300~3400 cm$^{-1}$ wide peak is ascribed to OH stretching vibration absorption in polyvinyl alcohol; the absorption peak at 2930 cm$^{-1}$ is ascribed to methylene $CH_2$ stretching vibration absorption; the 1710 cm$^{-1}$ belongs to C=O absorption peak in ester bond, and the 1185 cm$^{-1}$ and 1090 cm$^{-1}$ are characteristic absorption peaks of sulfonic acid group; NH bending vibration peak appears at 1570 cm$^{-1}$, C—N stretching vibration absorption peak appears at 1267 cm$^{-1}$, and C—O stretching vibration absorption peak appears at 1033 cm$^{-1}$, respectively.

2. Optical Micrograph

Figure 3:
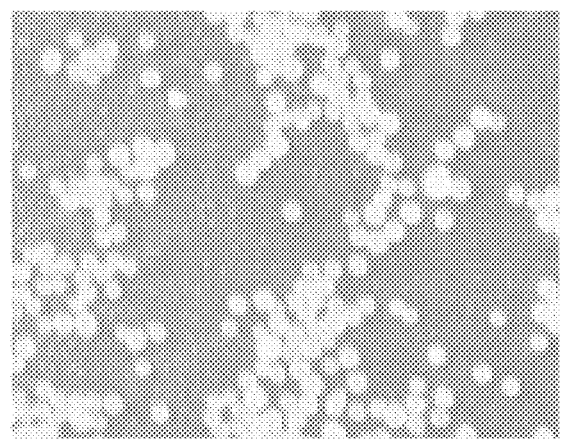
FIG. 3 Optical micrograph of the modified polyvinyl alcohol embolic microsphere of sample PVA-S-1

The modified PVA eluting microspheres PVA-S-1 in the swelling state are placed on the glass slide, adjusting the magnification of the optical microscope for observation of the morphology of the microspheres. The results in FIG. 3 show that the appearance of the microspheres is regular spherical and the color is bright white. There is no adhesion among the microspheres with diameter of 220-350 μm.

3. X-Ray Diffraction Pattern

Figure 4:
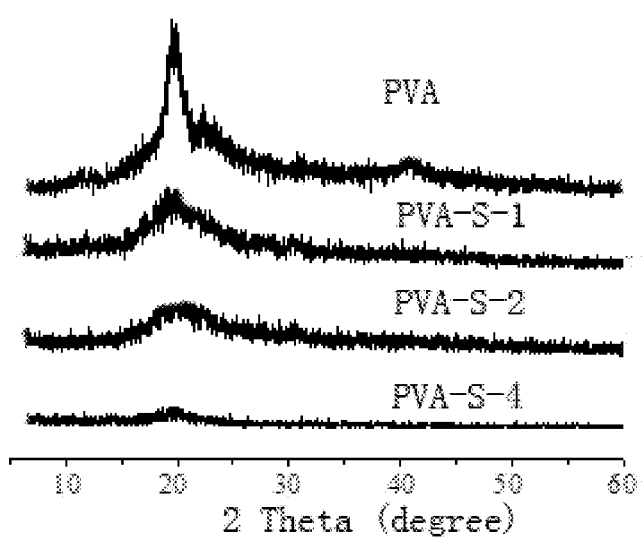
FIG. 4 X-ray diffraction pattern of PVA and the modified polyvinyl alcohol

The X-ray diffraction (XRD) results of PVA and modified polyvinyl alcohol are shown in FIG. 4. It can be seen that the crystal face (101) sharp diffraction peak of PVA appears at 19.7° (2θ). When the PVA is modified, the position of its characteristic diffraction peak is basically unchanged, but the strength is weakened and the peak shape is widened, which indicates that the crystal structure of PVA is consistent before and after modification, but the crystallinity is greatly reduced after modification. At the same time, it is found that with the increase of the modification degree, the intensity of the crystallization peak decreased significantly. This is because the introduction of taurine molecules into the side chain of PVA destroys the regularity of the PVA chain segment, so that the hydrogen bond association is weakened, and its crystallization capacity is reduced. Therefore, the crystal characteristics are weakened, indicating that the intensity of the diffraction peak decreased.

4. Swelling Property

Figure 5:
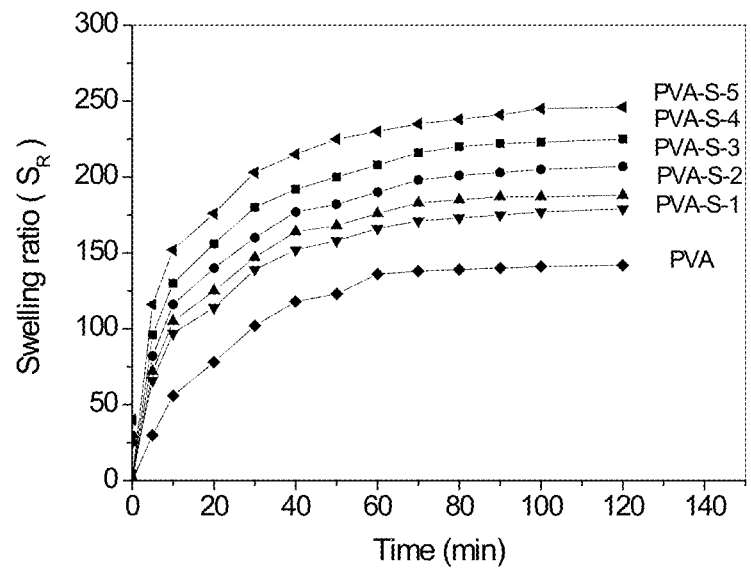
FIG. 5 Swelling performance of the modified polyvinyl alcohol embolic microspheres (in PBS buffer solution with pH=7.4)

The dried modified polyvinyl alcohol eluting microspheres are added to PBS buffer solution with pH=7.4 for swelling at a constant temperature of 37±0.5° C. The swelled microspheres are taken out at different time points, and are weighed. The swelling ratio SR (%) is calculated according to the following formula.

$$S_R(\%) = \frac{W_1 - W_0}{W_0} \times 100$$

Where $W_0$ and $W_1$ are the weights of the microspheres before and after swelling, respectively It can be seen from FIG. 5 that the swelling ratio of microspheres increases rapidly in the first one hour, then increases slowly, and reaches the equilibrium swelling within 2 h. With the increase of grafting degree of taurine in the microspheres, the swelling ratio of the microspheres increased from PVA-S-1 to PVA-S-5, because taurine molecules contain hydrophilic group of $SO_3H$, which leads to the increase of the swelling ratio of the microspheres in the swelling process. As a comparison, the swelling ratios of all modified samples are higher than that of the unmodified PVA microspheres. As described above, the hydrophilic groups of $SO_3H$ are introduced into the side chains of the modified PVA, which increases the water absorption performance.

Embodiment 8

Preparation of drug loaded modified PVA embolic microspheres: adding 30 mg of the modified PVA embolic microsphere to 6 mL of doxorubicin hydrochloride deionized water solution with a concentration of 4 mg/mL, filtering the microspheres after 5 hours reaction, washing the surface of the microspheres with deionized water, merging the washing solution into doxorubicin hydrochloride solution, measuring the absorbance of doxorubicin hydrochloride solution at 483 nm on an ultraviolet spectrophotometer, and calculating the drug loading rate of the microspheres. The microspheres are dried at 55° C. for 24 hours to obtain drug loaded embolic microspheres.

The drug loading rate ($L_R$) of microspheres is calculated according to the following formula:

$$L_R(\%) = \frac{W_D}{W_S} \times 100$$

Where $W_D$ is the mass of the drug adsorbed by the microspheres (mg); $W_S$ is the mass of the microspheres (mg).

Figure 6:
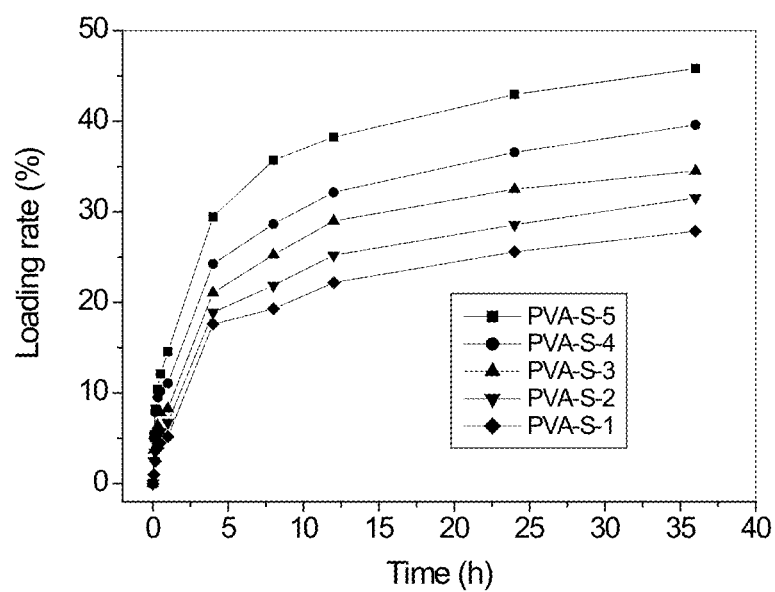
FIG. 6 Drug loading rate of the modified polyvinyl alcohol embolic microspheres at different times

FIG. 6 shows the drug loading kinetics curves of several modified PVA embolic microspheres in doxorubicin hydrochloride solution. It is observed that the drug loading rate and drug loading speed of the microspheres increased from PVA-S-1 to PVA-S-5. The high drug loading rate and loading speed are due to two reasons: first, sulfonic acid groups have been introduced into the modified PVA microspheres, the sulfonic acid groups and doxorubicin hydrochloride undergo an ion exchange drug loading mode, which directly improves the drug loading rate. Second, the introduction of taurine molecules into the side chain of PVA destroys the regular arrangement and partial crystallinity of PVA chain segments, increases the internal micropores and channels of the microspheres, and is also conducive to the diffusion of drug molecules. At the same time, the improvement of the internal structure of the microspheres also improves the efficiency of drug loading in physical ways. The combined effect of these factors leads to the improvement of drug loading rate and drug loading speed.

The invention claimed is:

1. A method for making modified polyvinyl alcohol embolic microspheres comprising:
   1) putting polyvinyl alcohol in organic solvent A and stirring for preparing a polyvinyl alcohol solution; dissolving acryloyl chloride or butenoyl chloride in organic solvent B for preparing an acyl chloride solution;
   2) adding an acid binding agent to the polyvinyl alcohol solution, dropping the acyl chloride solution into the polyvinyl alcohol solution, stirring for 3-5 hours at room temperature, then raising the temperature to 45-50° C., and stirring for additional 1-2 hours, cooling the reaction solution that results to room temperature, pouring the reaction solution into excess absolute ethanol for precipitating the polymer, then filtering, washing the polymer with absolute ethanol, drying the polymer to a constant weight in a drying oven, and obtaining allyl polyvinyl alcohol or butyryl polyvinyl alcohol;
   3) weighing the dried allyl polyvinyl alcohol or butyryl polyvinyl alcohol and putting it in water with stirring to dissolve it; then dissolving taurine in water to make a taurine solution, adding the taurine solution to the allyl polyvinyl alcohol solution or butyryl polyvinyl alcohol solution, adjusting the pH value to 9-11, stirring and reacting under temperature of 45-50° C. for 40-48 hours, then cooling the reaction solution that results to room temperature, slowly pouring the reaction solution into excess absolute ethanol for precipitating the product, filtering and washing the product with absolute ethanol, and drying the product in a drying oven to a constant weight to obtain functionalized modified polyvinyl alcohol;
   4) adding 3-5% by volume of a non-ionic surfactant to an oil for preparing an oil phase solution with even stirring; dissolving the functionalized modified polyvinyl alcohol in ionized water to prepare a solution with a functionalized modified polyvinyl alcohol concentration of 60-100 g/L, and then pouring it into the oil phase solution slowly for emulsification, adding a cross-linking agent when Tyndall phenomenon is observed, after 4-6 hours, demulsifying the emulsion with ethanol to obtain solid microspheres, filtrating and washing the microspheres with ethanol, and then drying to obtain modified polyvinyl alcohol embolic microspheres; wherein the organic solvent A in step 1) is one of dimethyl sulfoxide, N, N-dimethylacetamide or formamide; and the organic solvent B in step 1) is one of dichloromethane, trichloromethane or dichloroehane.

2. The method of claim 1, wherein in step 1), the polyvinyl alcohol is one of PVA124, PVA1799, PVA1750 or PVA1788.

3. The method of claim 1, wherein in step 1), the concentration of polyvinyl alcohol in the polyvinyl alcohol solution is 50-120 g/L and the concentration of acyl chloride in the acyl chloride solution is 80-150 g/L.

4. The method of claim 1, wherein in step 1), the molar ratio of polyvinyl alcohol to acryloyl chloride or butenoyl chloride is 1:0.2-1.

5. The method of claim 1, wherein in step 2), the acid binding agent is triethylamine or pyridine, and its dosage is 1-1.2 times the molar mass of the acryloyl chloride in step 1).

6. The method of claim 1, wherein in step 3), a ratio of dried allyl polyvinyl alcohol to taurine is 1:1-1.3.

7. The method of claim 1, wherein in step 4), the oil is one of paraffin oil, soybean oil or n-heptane; and the volume ratio of the functionalized modified polyvinyl alcohol solution to the oil phase solution is 1:4-7.

8. The method of claim 1, wherein in step 4), the cross-linking agent is a 25 wt % glutaraldehyde water solution or epichlorohydrin, and its weight accounts for 3-6% of the weight of the functionalized modified polyvinyl alcohol solution.

9. A method for carrying a drug, comprising loading microspheres prepared by the method of claim 1 with doxorubicin.

\* \* \* \* \*